United States Patent [19]
Poirier et al.

[11] Patent Number: 4,897,081
[45] Date of Patent: Jan. 30, 1990

[54] PERCUTANEOUS ACCESS DEVICE

[75] Inventors: Victor L. Poirier, Chelmsford; Warren C. Clay, Lynn; Benedict D. T. Daly, Wellesley, all of Mass.

[73] Assignees: Thermedics Inc., Woburn; TMCA Foundation Inc., Boston, both of Mass.

[21] Appl. No.: 15,588

[22] Filed: Feb. 17, 1987

Related U.S. Application Data

[63] Continuation of Ser. No. 613,931, May 25, 1984, abandoned.

[51] Int. Cl.⁴ .................. A61M 25/02; A61F 1/00
[52] U.S. Cl. ........................... 604/175; 604/93; 128/DIG. 26
[58] Field of Search .................. 604/175–180, 604/95; 128/DIG. 26

[56] References Cited

U.S. PATENT DOCUMENTS 3,783,868 1/1974 Bokros .
4,321,914 3/1988 Begovac et al. .
4,488,877 12/1984 Klein et al. .

FOREIGN PATENT DOCUMENTS 0010865 5/1980 European Pat. Off. ............ 604/175
0081724 6/1983 European Pat. Off. ............ 604/175
2056282 8/1979 United Kingdom .

OTHER PUBLICATIONS

Science Digest, "The Year's Top 100 Innovations and the Men and Women Behind Them", pp. 52, 64–65, Dec. 1985.

Primary Examiner—Stephen C. Pellegrino
Attorney, Agent, or Firm—Herbert E. Messenger

[57] ABSTRACT

Disclosed is a percutaneous access device (PAD) for long-term skin penetration and use as an access port in the body of a patient. The buttonlike device includes a flat skirt for subdermal anchoring of the PAD and a neck through which a tube may extend for transmission of materials to or from the body. A two-stage porous bed covering the skirt and at least a portion of the neck promotes formation of a tight, infection-free barrier between the percutaneous access device and adjacent tissues, stabilizing the device for long-term use. The first stage of the bed retards downgrowth of epidermal cells for a time sufficient for mature collagen to form in the second stage, thereby permitting the tight dermal/biomaterial interface or barrier to form at a location near the junction of the two stages.

3 Claims, 2 Drawing Sheets

PERCUTANEOUS ACCESS DEVICE

This application is a continuation of application Serial No. 613,931, filed May 25, 1984 now abandoned.

BACKGROUND OF THE INVENTION

Some of the subject matter disclosed herein is also disclosed in pending U.S. patent application Ser. No. 613,933, "Percutaneous Access Device With Removable Tube", filed May 25, 1984, in the name of Victor L. Poirier, now U.S. Pat. No. 4,668,222.

This invention relates to devices for permitting access to the body through the skin, i.e., percutaneous devices, and more particularly to skin penetration devices which may be used as an access port into the body for extended periods of time.

Percutaneous access devices are useful when frequent or long-term access to the body is required, as in kidney dialysis, drug delivery, intravenous feeding, ostomies, and transmission of energy to intracorporeal blood pumps. Practical devices for long-term skin penetration in humans, however, have not been successful prior to the present invention because skin adjacent to the implanted devices will not heal to form a tight barrier to infection. Instead, when a foreign device is implanted for percutaneous access, epidermal cells begin to migrate, each seeking to surround itself completely with other similar cells. The epidermal cells thus grow down the sides of the device in an attempt to expel it. Deep sinus tracts form and body fluids are exuded at the interface between the device and adjacent tissue, forming a bed for infection. The percutaneous device, if not expelled spontaneously, must be removed to allow the infection to be cured.

Another drawback of presently available skin penetration devices relates to the difficulty of correcting problems with tubes mounted to, and extending through, such devices. Catheter tubes which are used, for example, in continuous ambulatory peritoneal dialysis or continuous infusion of drugs may become misaligned, kinked, blocked, or coated with fibrin. With existing technology such catheters cannot readily be removed without disturbing the percutaneous access device, and thus they must be surgically removed and replaced with another access device at a different site. Current technology does not, therefore, readily permit multiple use of an implanted percutaneous access device wherein one catheter may be substituted for another, nor does it allow catheter removal followed by plugging of the device for use at a later time.

Accordingly, it is an object of the invention to provide an improved percutaneous access device.

It is an object of the invention to provide a percutaneous access device which promotes the formation of a tight barrier to infection and permits long-term skin penetration.

SUMMARY OF THE INVENTION

The invention concerns a percutaneous access device for long-term skin penetration in humans and animals. The device promotes formation of a tight barrier to infection by controlling the migration of epidermal cell downgrowth and providing a stable junction to insure mechanical and biologic stability.

According to the invention a percutaneous access device (PAD) is provided which in a preferred form resembles a button having a raised neck and a central hole or bore therethrough to accommodate a tube. The button includes a generally flat skirt and a neck integral with and substantially normal to the skirt. Both the skirt and neck are formed of a biocompatible material such as a semirigid polyurethane and are sized such that when the PAD is implanted its neck penetrates the epidermis and dermis and its skirt is anchored in the subcutaneous tissue.

A key feature of the percutaneous access device of the invention is a two-stage porous bed positioned along portions of the neck and skirt and which promotes the formation of a tight, infection-free barrier or biologic seal between the device and surrounding tissue. The bed includes a first stage formed of a material such as polytetrafluoroethylene (PTFE) having pores of a specified size and having a specified path length. The first stage covers at least a lower portion of the neck and extends along a curved transition zone between neck and skirt and preferably along an adjoining portion of the skirt. A second, more porous stage of the bed, formed of a material such as a polyester velour, covers at least some, and desirably all, of the remainder of the skirt and forms a critical junction with the first stage. The path length of the first stage along the neck and skirt and the pore sizes of both stages of the porous bed are selected such that, upon implantation of the skirt in subcutaneous tissue, the first stage permits a controlled rate of downward growth of epidermal cells while the second stage promotes formation of collagen and its displacement of body fluids in the large pores of the second stage. In a preferred form of the invention, the first stage has a path length of about 0.25 inches and includes pores about 75–125 microns in size, and the second stage includes pores about 400–800 microns in size. By the time epidermal downgrowth reaches the junction between the first and second stages of the bed, mature collagen has formed in the second stage, causing epidermal cell downgrowth and sinus tract penetration to cease and a tight, infection-free seal to form at or near the junction. The tight dermal/biomaterial barrier stabilizes the implanted percutaneous access device, permitting its long-term use in the body.

DESCRIPTION OF PREFERRED EMBODIMENTS

The long-term percutaneous access device (PAD) shown and described herein overcomes the fundamental instability of known devices in that it promotes the formation of a tight, infection-free barrier. The biologic barrier or seal is formed in a predetermined area adjacent to the device by the use of a unique two-stage bed of controlled porosity and length covering the main structural body of the percutaneous access device.

Figure 1:
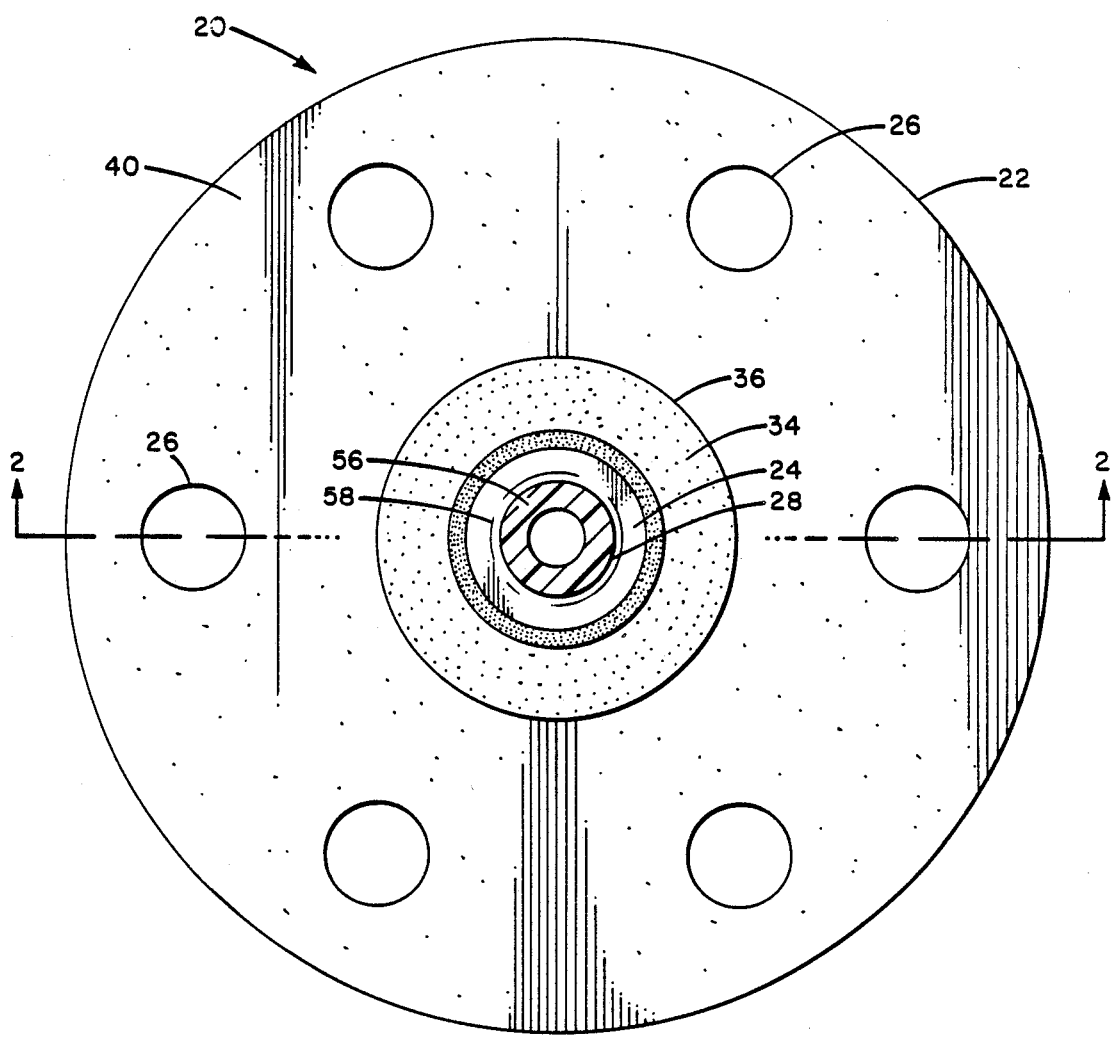
FIG. 1 is a top or plan view of a preferred percutaneous access device (PAD) described herein.
Figure 2:
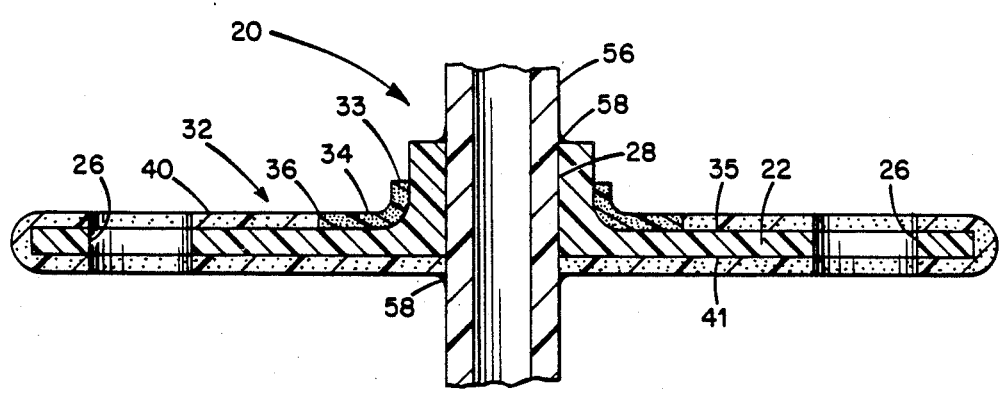
FIG. 2 is a cross-sectional view of the device of FIG. 1 taken along the line 2—2.
Figure 4:
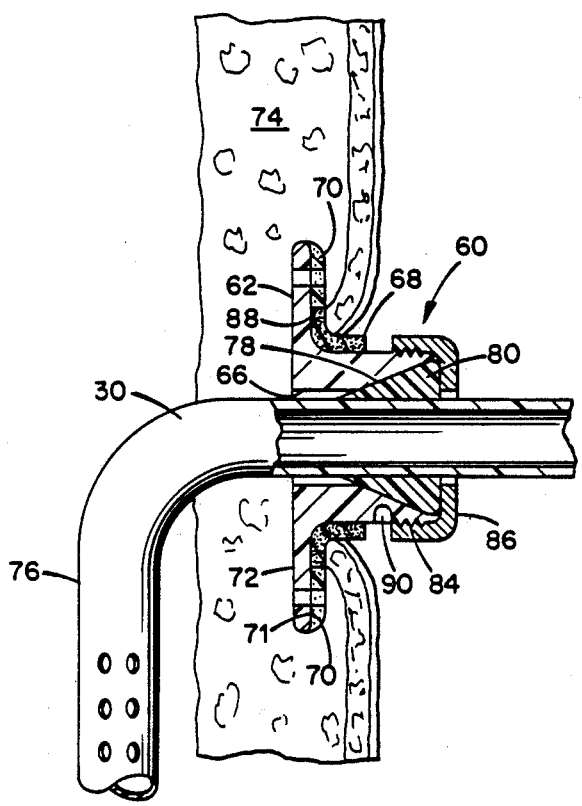
FIG. 4 is a cross-sectional view of a percutaneous access device illustrating a tube-mounting arrangement permitting removal and replacement of tubes extending through the implanted device.

A preferred percutaneous device 20 for implantation in humans is shown in FIGS. 1 and 2. The PAD 20 is buttonlike in appearance and includes a generally flat flange or skirt 22 for anchoring the device and a hub or neck 24, preferably integral with and generally normal to the skirt 22. The skirt 22 and the neck 24 are formed of a nontoxic biocompatible semiflexible material such as a semirigid polyurethane. A suitable polyurethane is Tecoflex EG-60D, available from Thermedics Inc. of Woburn, Mass. Preferably the skirt 22 is disk-shaped and has a diameter in the range of about 1.2 to 1.8 inches and a thickness of about 0.010 to 0.100 inches. One or more holes 26 are provided in the skirt 22 to encourage tissue penetration for increased anchoring of the PAD 20, to facilitate lymphatic drainage, and to reduce swelling. The neck 24 has a diameter of about 0.25 to 0.50 inches and flares upward from the skirt 22 a distance of about 0.08 to 0.40 inches so as to extend through the epidermal and dermal layers of a patient when the skirt 22 is implanted in the subcutaneous tissue (see FIG. 4). A central hole or bore 28 is provided in the neck 24 and also extends through the skirt 22 to accommodate a tube 30 (FIG. 4).

To promote healing of skin and the formation of a tight, infection-free barrier between the percutaneous access device 20 and adjacent tissues following implantation of the PAD 20, the skirt 22 and at least the lower portion of the neck 24 are covered by a two-stage porous bed 32. A first stage 34 of the bed 32 overlies the lower portion of the neck 24, preferably commencing at a location such that the top 33 of this first stage 34 is positioned just below the epidermal layer when the PAD is implanted. The first stage 34 also extends along part of the upper surface 35 of the skirt 22—e.g., a distance of about 0.10 to 0.25 inches, terminating at a junction 36 formed between adjacent ends of the first stage 34 and a second stage 40.

A preferred material for the first stage 34 of the porous bed is polytetrafluoroethylene (PTFE) having pore sizes of about 50–125 microns and a thickness of about 0.020 inches. For example, the first stage of the porous bed may be formed of Impra 15:1, a PTFE material available from Impra Inc., of Tempe, Ariz., and formed by extrusion followed by stretching to fifteen times the extruded length. The second stage 40 of the porous bed 32 covers at least the remainder of the upper surface 35 of the skirt 22 and preferably the lower surface 41 as well. This stage 40 of the porous bed 32 may be formed of a material such as a polyester velour (e.g. Dacron velour available as part No. 600K61121 available from the United States Catheter and Instrument Company of Glenfalls, N.Y.) This material is a woven fabric with loose strands to allow for cell infiltration, and its pore sizes are considerably larger than those of the first stage 34 of the porous bed 32, typical values being about 400 to 800 microns.

Both porous stages are tightly bonded to the underlying substrate (the skirt 22 and the neck 24) by a suitable adhesive such as No. 1-MP polyurethane adhesive available from Thermedics Inc. of Woburn, Mass. To improve its adhesion to the skirt 22 the Dacron velour may be chemically stripped, as by washing it in distilled water adjusted to a ph of 10.

It is essential to the successful long-term implantation of the percutaneous access device of the invention that the path length of the first stage 34 of the porous bed 32 along the neck 22 and the skirt 24, and the pore sizes of both stages 34 and 40, be properly selected to fulfill the different functions performed by these stages. Accordingly, the material of the first stage 34 has pores of about 50–125 microns in size, preferably about 75–125 microns, a size which permits downgrowth of epidermal cells, but at a rate far less than would occur in a material having larger pores. The biomaterial of the second stage has pores of about 400 to 800 microns in size, large enough to allow penetration and viability of cells such as fibroblasts which displace body fluids from these pores and synthesize collagen. The controlled rate of epidermal cell downgrowth allowed by the first stage 34, together with a first stage length of about 0.25 inches, is sufficient to prevent epidermal cells from reaching the junction 36 between the stages 34 and 40 until mature collagen is formed in the pores of the second stage 40 (typically two to six months following implantation of the device 20). The presence of mature collagen in the second stage 40 terminates the growth of epidermal cells at or near the junction 36, thus forming a stable, tight, dermal/biomaterial barrier.

For purposes of the invention described and claimed herein, pore size is defined as the diameter of a circle whose area is equal to the area of an equivalent opening or void in the bed structures. The pores may, for example, be formed between threads or filaments of the porous bed structures, the filaments preferably being utilized in multiple layers positioned in random fashion to avoid alignment of pores in adjacent layers. The resulting structure of the porous bed stages has voids or pores which are interconnected in tortuous paths along the length of the bed, permitting controlled growth of cells through the pores and strong mechanical bonding due to wrapping of cells around the filaments. It is essential that the pores be interconnected so that cells may infiltrate and, particularly with reference to the first stage of the porous bed, so that epidermal cells may grow down through the pores of the first stage at a controlled rate.

The necessity of proper pore size selection and of a two-stage bed of porous material is indicated by the following discussion of the consequences of alternative structures. For example, were a single stage bed of small pore size material utilized in the percutaneous access device 20, such pores would not permit survival of infiltrating fibroblasts and the formation of mature collagen needed to halt the growth of epidermal cells. Were a single stage bed of large pore size material utilized, body fluids would be wicked to the external environment, providing a moist environment for bacterial infection. Note that even in a two-stage bed, use in the first stage of material having pores which are too small will not sufficiently retard epidermal cell downgrowth since rapid downgrowth of epidermal cells will occur around the first stage. In each of the above-noted alternatives no stable, infection-free barrier would form to permit long-term implantation of the percutaneous access device.

Figure 3:
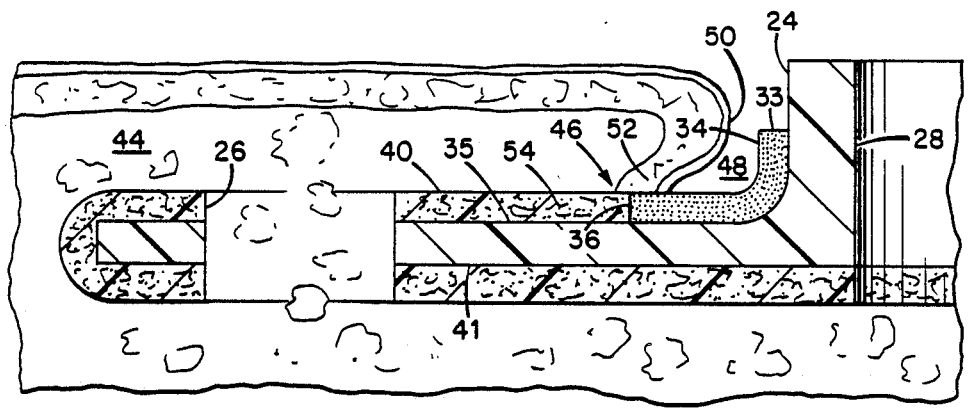
FIG. 3 is an enlarged cross-sectional view of one-half of a preferred percutaneous device illustrating in schematic form the histology associated with a stabilized, implanted PAD.

FIG. 3 shows in diagram form the skin and tissue structure adjacent to a stabilized implanted percutaneous access device 44 as disclosed herein. For ease of illustration, only one-half of the symmetrical PAD 20 is indicated and no tube is shown extending through the central bore 28. The histology illustrated, which is typical of that observed about six months after implantation of the device 20 in the subcutaneous layer 44, is characterized by a stable interface 46 between the skin and the PAD 20. The interface or barrier 46 is located near the junction 36 between the PTFE first stage 34 and the polyester velour second stage 40 of the porous bed and lies at the end of a sinus 48 which forms and progresses downward and along the porous bed 32 during the 2–6 month period of stabilization of the implanted device 20. A thin epidermal layer 50 lines the sinus 48, and the connective tissue 52 in the interface 46 is similar to dermis. Mature collagen bundles 54 are present in the polyester velour second stage 40, and the implant site is generally infection-free. The interface 46 remains essentially stable for periods of one year or longer.

Percutaneous access devices having the general configuration shown in FIGS. 1–3 (but without a central bore 28 and tube) were implanted in various positions of pigs and many survived a full year before being electively explanted. Examination of the connective tissue of these devices showed structure similar to that of FIG. 3, including an interface near the junction of the two stages of the porous bed having mature dense collagen similar to dermis.

The first stage 34 of the porous bed may, instead of being formed of PTFE, be fabricated of multiple layers of filaments of a polyurethane such as Tecoflex® EG-60D, available from Thermedics Inc. of Woburn, Mass. (Tecoflex is a registered trademark of Thermedics for medical grade urethane elastomeric materials). This polyurethane, which is formed as the reaction product of dicyclohexyl methane diisocyanate, polytetramethylene ether glycol, and 1, 4 butane diol, has shown excellent cell attachment characteristics and biocompatibility in invitro tests of several biomaterials with human skin fibroblasts. When used in the first stage of the porous bed, the filaments preferably have a diameter of from about 0.004 to 0.015 inches and are formed into a structure having about three to ten layers. The structure is fabricated such that it has spaces or open areas between filaments of about 0.001 to 0.004 inches (as measured from electron micrographs of surfaces and cross-sections of the porous bed). One method of fabricating the first stage 34 of the porous bed is to wind in random fashion the polyurethane filaments onto a mandrel and then to form a bonded structure by heating the mandrel—for example, to a temperature of about 110° C. for approximately one half hour. An alternative to heating the wound filaments is to overcoat them with an adhesive such as a dilute solution of the polyurethane Tecoflex EG-60D plus a solvent.

Tecoflex EG-60D polyurethane may also be used in the second stage of the porous bed in place of Dacron velour. A suitable loose mesh structure includes about 3 to 10 layers of filaments of 0.004 to 0.015 inch diameter formed with interfilament spacings of about 0.015 to 0.030 inches. Also, the filaments may be reinforced with a higher modulus core such as Dacron.

As suggested in FIG. 2, the percutaneous access device 20 can be assembled prior to implant with an appropriate catheter 56. A permanent seal or bond 58 can be accomplished by using an adhesive such as 1-MP polyurethane adhesive available from Thermedics, Inc. of Woburn, Mass.

Figure 5:
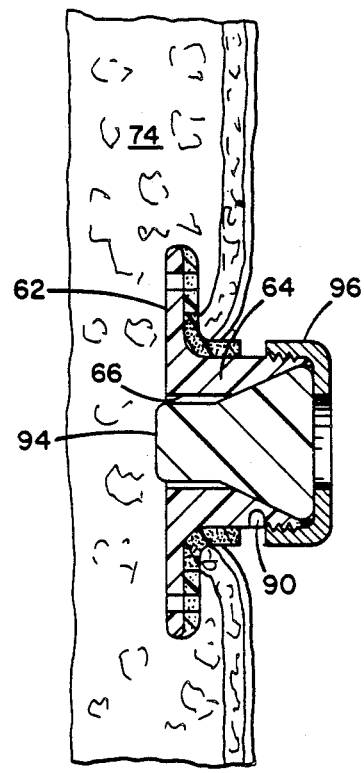
FIG. 5 is a cross-sectional view of an implanted percutaneous access device which is plugged for further potential use.

FIGS. 4 and 5 illustrate a percutaneous access device which facilitates replacement and removal of tubes in a PAD without the need for surgery and with minimal interference with an implanted PAD. Non-surgical removal of catheters may be particularly desirable for replacement of kinked, blocked, or misaligned catheters or for multiple use of a single, permanently-implanted PAD. The percutaneous access device 60 shown in FIG. 4, as in the earlier-described PAD, has a button-like main body including a skirt 62 and a neck 64 with a bore 66 therethrough. Portions of the neck 64 and the skirt 62 are covered by a porous bed which preferably comprises a first stage 68 and an adjoining second stage 70. The second stage 70 of the porous bed may cover just the upper surface 71 of the skirt 62 as shown in FIGS. 4 and 5 or it may also cover the lower surface 72 as in the device illustrated in FIGS. 1–3. The device 60 as shown has its skirt 62 implanted in the subcutaneous tissue 74 of an abdominal wall of a patient with a catheter 30 mounted to and extending through the PAD and having its implanted end 76 directed generally downward.

To permit mounting of the catheter 30 to, and its removal from, the percutaneous access device 60, the PAD 60 includes a connector lock, a preferred type being the screw ring lock illustrated in FIGS. 4 and 5, but which may instead comprise other forms of twist locks or connectors which can be operated with minimal disturbance of the implanted device 60. In conjunction with the lock shown in FIG. 4, the neck 64 of the PAD 60 includes a tapered portion 78 which accommodates a seal 80. The seal 80 may, for example, be formed of an elastomeric body which fits over the tube 30 and is shaped to fill the enlarged portion of the bore 66. The end of the neck opposite the skirt 62 also has a threaded outer surface 84 to engage a screw ring 86 which fits over the catheter 30 and, when tightened, presses the seal 80 against the neck 64 and the tube 30. A metallic insert such as titanium may be used to insure proper attachment of the screw ring or connector lock.

It is important for re-use of the percutaneous access device 60 illustrated in FIGS. 4 and 5 that there be minimal disturbance to the interface between the PAD 60 and adjacent tissue during removal and replacement of the tube 30, and particularly that the infection-free barrier formed near the junction 88 between stages 68 and 70 of the porous bed not be broken. To minimize such disturbance, two or more recesses or indentations 90 may be provided in the outer circumference of the neck 64 of the PAD 60 adjacent to the threaded surface 84 so that during tightening or removal of the screw ring 86 the neck 64 may be tightly restrained against twisting by means of a spanner wrench having gripping elements receivable in the indentations 90.

FIG. 5 shows a percutaneous access device 60 which carries a plug 94 instead of a catheter, a configuration which may be desirable for patients not requiring a catheter on a continuous basis, but for whom periodic or future use of a catheter is likely. The plug 94, which is preferably formed of a biocompatible elastomeric material, may be retained by a non-perforated screw cap 96 as illustrated in FIG. 5, or the screw ring 86 shown in FIG. 4 or any other suitable holder may be employed.

It is to be understood that the forms of the percutaneous access device shown and described herein are preferred embodiments and that the device may be constructed of various other biocompatible materials and with some change in shape and size without departing from the spirit or scope of the invention. The invention is defined as all embodiments and their equivalents within the scope of the claims which follow.

What is claimed is:

1. In a percutaneous access deice including a button having a skirt and a neck integral with and substantially normal to said skirt, said neck and skirt being formed of a semirigid biocompatible material and having a bore therethrough to accommodate a tube, and a porous bed overlying and attached to at least a portion of said button, the improvement wherein said porous bed comprises a first stage extending along a portion of said skirt adjacent to said neck and along at least the lower portion of said neck and a second stage formed essentially of a biocompatible material and having pores of a size in the range of about 400–800 microns, said first stage having a total length along said neck and said skirt of at least 0.25 inches and being fabricated of layers of filaments of a diameter in the range of about 0.0004 to 0.015 inches and of a polyurethane material which is the reaction product of dicyclohexyl methane diisocyanate, polytetramethylene ether glycol, and 1,4 butane diol, said layers being formed into a structure having pores of a size in the range of about 50–125 microns, said percutaneous access device, upon implantation of the skirt in subcutaneous tissue adjacent to the dermis, promoting formation of a stable, tight, infection-free biologic seal between said device and adjoining tissue through the downgrowth of epidermal cells through the first stage and the formation of mature collagen in said second stage.

2. A percutaneous access device as in claim 1 wherein said second stage comprises layers of filaments of a polyurethane material formed as the reaction product of dicylohexyl methane diisocyanate, polytetramethylene ether glycol, and 1,4 butane diol.

3. A percutaneous access device implantable in humans for periods of up to a year or longer to permit access to the body through the skin comprising:

a main body including a substantially flat, disk-shaped skirt and a neck integral with and substantially normal to said skirt, said neck and skirt formed of a biocompatible polyurethane and including a bore therethrough to accommodate a tube; to a lower a first porous bed surrounding and attached portion of said neck and extending along a portion of the upper surface of said skirt adjacent to said neck, said first porous bed being formed of a polyurethane material which is the reaction product of dicyclohexyl methane diisocyanate, polytetramethylene ether glycol, and 1,4 butane diol and including a multiplicity of interconnected pores having a size in the range of about 50–125 microns so that upon implantation of the skirt just below the dermis, said pores permit downgrowth of epidermal cells through said bed at a controlled rate substantially without allowing wicking of body fluids upward to a point external to the body; and a second porous bed forming a junction on said skirt with one end of said first bed, said second porous bed attached to and covering the portion of the skirt not overlain by said first bed and including pores of a size in the range of about 400–800 microns so as to permit infiltration of fibroblasts and formation of collagen in said pores;

said beds promoting the formation of a stable, tight, infection-free biologic seal between said beds and adjoining tissue.

* * * * *